United States Patent [19]
Whittaker

[11] Patent Number: 5,409,937
[45] Date of Patent: Apr. 25, 1995

[54] HEXAHYDROFURO(2,3-B)FURANS AS PAF ANTAGONISTS

[75] Inventor: Mark Whittaker, Oxford, England

[73] Assignee: British Biotech Pharmaceuticals Limited, Oxford, England

[21] Appl. No.: 211,795

[22] PCT Filed: Oct. 21, 1992

[86] PCT No.: PCT/GB92/01931
§ 371 Date: Apr. 18, 1994
§ 102(e) Date: Apr. 18, 1994

[87] PCT Pub. No.: WO93/08194
PCT Pub. Date: Apr. 29, 1993

[30] Foreign Application Priority Data
Oct. 21, 1991 [GB] United Kingdom ............. 9122308

[51] Int. Cl.6 .................. A61K 31/435; A61K 31/44; C07D 471/04; C07D 493/04
[52] U.S. Cl. ................... 514/303; 514/338; 514/394; 546/118; 546/197; 548/305.1
[58] Field of Search ............. 546/118, 197; 548/305.1; 514/303, 338, 394

[56] References Cited
U.S. PATENT DOCUMENTS
4,888,337 12/1989 Godfroid et al. ............. 514/326

FOREIGN PATENT DOCUMENTS
0144804A2 6/1985 European Pat. Off. .
0199324A2 10/1986 European Pat. Off. .
0238202A2 9/1987 European Pat. Off. .
WO90/09997 9/1990 WIPO .
WO91/17157 11/1991 WIPO .
WO92/03422 3/1992 WIPO .
WO92/03423 3/1992 WIPO .

OTHER PUBLICATIONS
Cooper et al. (1992), *J. Med. Chem.*, vol. 35, pp. 3115–3129.
Weinreb et al. (1982), *J. Am. Chem. Sco.*, vol. 104, pp. 536–544.
Whittaker et al. (1992), *Curr. Opin. Thera. Patents*, vol. 2, pp. 583–623.

Primary Examiner—Bernard Dentz
Attorney, Agent, or Firm—Allegretti & Witcoff, Ltd.

[57] ABSTRACT

The invention concerns compounds of the formula I:

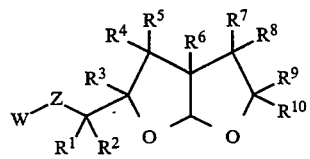

wherein the variables are described in the specification which are antagonists of platelet activity factor.

8 Claims, No Drawings

HEXAHYDROFURO(2,3-B)FURANS AS PAF ANTAGONISTS

This application is filed under 35 USC 371 based on PCT/GB 92/01931 filed Oct. 21, 1992.

This invention relates primarily to novel compounds which are antagonists of platelet activating factor.

Platelet Activating Factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds that have been disclosed as possessing activity as PAF antagonists include compounds which are structurally related to the PAF molecule such as glycerol derivatives (EP-A-0238202), and heterocyclic compounds such as 5-oxy derivatives of tetrahydrofuran (U.S. Pat. No. 4,888,337) and 2,5-diaryl tetrahydrofurans (EP-A-0144804). Recently a more potent 2,5-diaryl tetrahydrofurans derivative, (trans)-2-(3-methoxy-5-methylsulphonyl-4-propoxyphenyl)-5-(3,4,5-trimethoxyphenyl)tetrahydrofuran (L-659,989) has been disclosed (EP-A-0199324). In our International patent application no. WO 91/17157 we disclose a series of γ-butyrolactol derivatives as PAF antagonists. The compounds of WO 91/17157 differ from the 5-oxy derivatives of tetrahydofuran described in U.S. Pat. No. 4,888,337 and from the 2,5-diaryl tetrahydrofurans such as L-659,989, in that they feature an appended heterocycle with an unsubstituted sp² nitrogen atom. There are a number of other PAF antagonists, in addition to those of WO 91/17157, for which the presence of a heterocyclic sp² nitrogen atom appears to be an important requirement for activity (Whittaker, M., Curr. Opin. Thera. Patents 2(5), 583–623 (1992)).

For the compounds of the present invention the presence of a heterocyclic group possessing an unsubstituted sp² nitrogen atom is also a requirement for PAF antagonist activity. However, the compounds of the present invention differ from the other PAF antagonists refered to above in that they are hexahydrofuro[2,3-b]furan derivatives.

The present invention provides novel and useful substituted hexahydrofuro[2,3-b]furan derivatives and their pharmaceutically acceptable acid addition salts, and pharmaceutical uses thereof as PAF antagonists.

According to a first aspect of the invention there is provided a compound of general formula I;

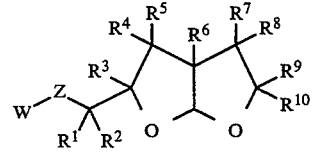

wherein:
W represents pyrid-3-yl, benzimidazol-1-yl, and imidazo[4,5-c]pyrid-1-yl optionally substituted with one or more substituents selected from methyl, methoxy, halo, —CF$_3$ and —CN—.
Z represents
  a) a bond;
  b) a divalent alkanediyl group from 1 to 4 carbon atoms which may be a straight or branched-chain, wherein the said group is either unsubstituted or substituted by one or more substituents selected from hydroxy, —OC$_1$-C$_6$ alkyl, —SC$_1$-C$_6$ alkyl, —CN and halo;
  c) a divalent alkenediyl or alkynediyl group from 2 to 4 carbon atoms which may be a straight or branched-chain, wherein the said group is either unsubstituted or substituted by one or more substituents selected from hydroxy, —OC$_1$-C$_6$ alkyl, —SC$_1$-C$_6$ alkyl, —CN and halo;
  d) a —(CH$_2$)$_q$U(CH$_2$)$_r$— group, optionally substituted by —CN, wherein q is an integer from 0-2, r is an integer from 0-2 and U represents a sulphur atom, an oxygen atom, a —N(H)— group, a —N(C$_1$-C$_6$ alkyl)— group, a —N(CH$_2$CH$_2$NMe$_2$)— group or a —N(C(=O)C$_1$-C$_6$ alkyl)— group;
R$^1$, R$^2$, R$^3$, R$^4$, R$^5$, R$^6$, R$^7$, R$^8$ and R$^9$ each independently represents hydrogen, halo, —OH, —C$_1$-C$_6$ alkyl;
R$^{10}$ represents —C$_1$-C$_{18}$ alkyl, —C$_2$-C$_{18}$ alkenyl, —C$_3$-C$_8$ cycloalkyl, —C$_4$-C$_8$ cycloalkenyl, a —V group, where V is a

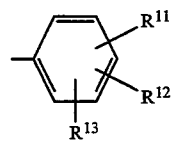

group wherein each of R$^{11}$, R$^{12}$ and R$^{13}$ is independently hydrogen, —C$_1$-C$_6$ alkyl, —OC$_1$-C$_6$ alkyl, —SC$_1$-C$_6$ alkyl, halo, —CN, —NO$_2$, —SOC$_1$-C$_6$ alkyl, —SO$_2$C$_1$-C$_6$ alkyl, —SO$_2$(CH$_2$)$_{1-4}$CH$_2$OH, —SO$_2$NH$_2$, —CO$_2$H, —CO$_2$C$_1$-C$_6$ alkyl, —CHO, —COC$_1$-C$_6$ alkyl, —CH$_2$OH, —OH, benzyl, benzoyl, —CF$_3$, —CONH$_2$, —NHCOC$_1$-C$_6$ alkyl, or an —NR$^{14}$R$^{15}$ group wherein each of R$^{14}$ and R$^{15}$ is independently hydrogen or —C$_1$-C$_6$ alkyl;
or a pharmaceutically or veterinarily acceptable acid addition salt or hydrate thereof.

As used herein the term "halo" means fluoro, chloro, bromo or iodo.

As used herein the term "C$_1$-C$_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "$C_1$–$C_{18}$ alkyl" refers to straight chain or branched chain hydrocarbon groups having from one to eighteen carbon atoms.

Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to eight carbon atoms may be preferred.

As used herein the term "$C_2$–$C_{18}$ alkenyl" refers to straight chain or branched chain hydrocarbon groups having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl, and farnesyl. From two to eight carbon atoms may be preferred.

As used herein the term "$OC_1$–$C_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$SC_1$–$C_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$–$C_8$ cycloalkyl" refers to an alicyclic group from 3 to 8 carbon atoms. Illustrative of such cycloalkyl groups are cyclopropyl, cyclobutyl, cyclopentyl and cyclohexyl.

As used herein, the term "$C_4$–$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "alkanediyl" refers to a disubstituted straight or branched saturated hydrocarbon chain.

As used herein, the term "alkenediyl" refers to a disubstituted straight or branched hydrocarbon chain having one or more double bonds and the term "alkynediyl" refers to a disubstituted straight or branched hydrocarbon chain having one or more triple bonds.

Hereafter in this specification the term "compound" includes "salt" or "hydrate" unless the context requires otherwise.

In compounds of this invention, the presence of several asymmetric carbon atoms gives rise to diastereoisomers, each of which consists of two enantiomers. With the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

It is considered that the main structural features of compounds of general formula I that are particularly significant in providing their PAF antagonist activity, are the sp² nitrogen heterocycle (W group), the two oxygen atoms of the hexahydrofuro[2,3-b]furan and the aliphatic or aromatic hydrocarbon group $R^{10}$. The spatial orientation of these key groupings is controlled by the

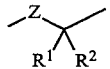

linkeage between the sp² nitrogen heterocycle and the hexahydrofuro]2,3-b]furan ring system. The nature or identity of the hexahydrofuro[2,3 -b]furan substituents $R^3$–$R^9$ inclusive may be changed within the scope of the invention with retention of PAF antagonist activity. Likewise, there may be considerable variation of the length of the hydrocarbon chain $R^{10}$ or (where $R^{10}$ is a substituted aromatic hydrocarbon group) of the nature and identity of the defined phenyl ring substituents $R^{11}$–$R^{13}$. Variation of these options within the scope of the structural definition given for general formula I provides compounds that retain PAF antagonist activity.

The group W of general formula I is an sp² nitrogen heterocycle that is important for PAF antagonist activity. From the structure-activity relationships for the compounds disclosed in our previous patent applications (WO 90/09997, WO 91/17157, WO 92/03422 and WO 92/03423) it is apparent that the sp² nitrogen heterocycles which are claimed here for W (pyrid-3-yl, benzimidazol-1-yl, and imidazo[4,5-c]pyrid-1-yl each of which may be optionally substituted) are particularly suitable for providing PAF antagonist activity. However, it is understood that compounds of general formula I in which W is a sp² nitrogen heterocycle other than those claimed here may also possess activity as PAF antagonists. The variety of sp² nitrogen heterocycles that could provide PAF antagonist activity include those disclosed in our patent application WO 91/17157 and those recently described by Whittaker (Whittaker, M., Curr. Opin. Thera. Patents 2(5), 583–623 (1992)) and Cooper (Cooper, K., et al., J. Med. Chem. 35(7), 3115–3129 (1992)). The exact nature of the interaction of the sp² nitrogen heterocycle and the receptor has not been determined, but it would appear that it is important for the heterocycle to possess at least one unsubstituted sp² nitrogen atom within the heterocyclic ring.

Preferred compounds include those in which, independently or in any compatible combination:

W represents a pyrid-3-yl (for example pyrid-3-yl and 2-methylpyrid-3-yl) group, a benzimidazol-1-yl (for example 2-methylbenzimidazol-1-yl), or a imidazo[4,5-c]pyrid-1-yl (for example 2-methylimidazo[4,5-c]pyrid-1-yl) group;

Z represents a bond, a divalent alkanediyl (for example methylene and ethylene) group or a —($CH_2$)$_q$U($CH_2$)$_r$— (substitued by —CN) group;

q represents an integer of 1;

r is an integer of 0 or 1;

U represents a —N(H)— group, a —N($C_1$-$C_6$ alkyl)— (for example —N(Me)—) group or a —N($CH_2CH_2NMe_2$)— group;

$R^1$ represents a hydrogen atom;
$R^2$ represents a hydrogen atom;
$R^3$ represents a hydrogen atom;
$R^4$ represents a hydrogen atom;
$R^5$ represents a hydrogen atom;

$R^6$ represents a hydrogen atom:
$R^7$ represents a hydrogen atom;
$R^8$ represents a hydrogen atom;
$R^9$ represents a hydrogen atom;
$R^{10}$ represents a —$C_1$–$C_{18}$ alkyl (for example pentadecyl) group or a V group;
$R^{11}$ represents a —$C_1$–$C_6$ alkyl (for example isopropyl) group, a halogen (for example fluorine and chlorine) atom or a —$OC_1$–$C_6$ alkyl (for example methoxy) group;
$R^{12}$ represents a hydrogen atom, a —$C_1$–$C_6$ alkyl (for example isopropyl) group, a halogen (for example chlorine) atom or a —$OC_1$–$C_6$ alkyl (for example methoxy) group;
$R^{13}$ represents a hydrogen atom, a —$C_1$–$C_6$ alkyl (for example isopropyl) group or a —$OC_1$–$C_6$ alkyl (for example methoxy) group.

Particularly preferred compounds include:
1. 5-(4-Fluorophenyl)-2-(1H-2-methylbenzimidazol-1-ylmethyl)hexahydrofuro[2,3-b]furan,
2. 5-(4-Fluorophenyl)-2-(1H-2-methylimidazo[4,5-c]pyrid-1-ylmethyl)hexahydrofuro[2,3-b]furan,
3. 2-(4-Fluorophenyl)-5-(2(1H-2-methylimidazo[4,5-c]pyrid-1-yl)ethyl)hexahydrofuro[2,3-b]furan,
4. 2-(4-Methoxyphenyl)-5-(2(1H-2-methylimidazo[4,5-c]pyrid-1-yl)ethyl)hexahydrofuro[2,3 -b]furan,
5. 2-(3,4-Dimethoxyphenyl)-5-(2(1H-2-methylimidazo[4,5-c]pyrid-1-yl)ethyl)hexahydrofuro[2,3-b]furan,
6. 2-(3,4-Dichlorophenyl)-5-(2(1H-2-methylimidazo[4,5-c]pyrid-1-yl)ethyl)hexahydrofuro[2,3-b]furan,
7. 2-(3-Chloro-4-methoxyphenyl)-5-(2(1H-2-methylimidazo[4,5-c]pyrid-1-yl)ethyl)hexahydrofuro[2,3-b]furan,
8. 2-(2,4,6-Triisopropylphenyl)-5-(2(1H-2-methylimidazo[4,5-c]pyrid-1-yl)ethyl)hexahydrofuro(2,3-b]furan,
9. 2-(2(1H-2-Methylimidazo[4,5-c]pyrid-1-yl)ethyl)-5-pentadecylhexahydrofuro[2,3-b]furan,
10. 2-(4-Fluorophenyl)-5-[N-(3-pyridylcyanomethyl)aminoethyl]hexahydrofuro[2,3-b]furan,
11. 5-[N-((2-Methyl)-3-pyridylcyanomethyl)aminoethyl]-2-(3,4,5-trimethoxyphenyl)hexahydrofuro[2,3-b]-furan,
12. 5-(4-Fluorophenyl)-2-[N-(3-pyridylcyanomethyl)aminomethylhexahydrofuro[3-b]furan,
13. 5-(4-Fluorophenyl)-2-1? -(3-pyridylcyanomethyl)-N-(N',N'-dimethylaminoethyl)aminomethyl]hexahydrofuro[2,3-b]furan.

Compounds of general formula I may be prepared by any suitable method known in the art and/or by the following process, which itself forms part of the invention.

According to a second aspect of the invention, there is provided a process for preparing a compound of general formula I as defined above, the process comprising:
a) treating a hexahydrofuro[2,3-b]furan derivative represented by the general formula II

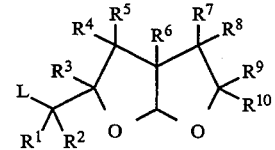

wherein $R^1$, $R^2$, $R^3$, $R^4$, $R^5$, $R^6$, $R^7$, $R^8$, $R^9$, and $R^{10}$ are as defined in general formula I and L is a leaving group such as bromo or iodo, with a compound of the general formula III

wherein W and Z are as defined in general formula I, or b) treating a hexahydrofuro[2,3-b]furan compound represented by the general formula IV

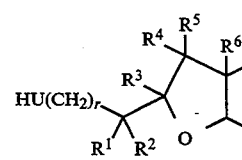

wherein $R^1$, $R^2$, $R^3$, $R^4$, $R^5$, $R^6$, $R^7$, $R^8$, $R^9$, $R^{10}$, r and U are as defined in general formula I with a compound of general formula V

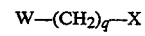

wherein W and q are as defined in general formula I and X is a leaving group such as fluoro, chloro, bromo, iodo, methanesulphonyloxy, p-toluenesulphonyloxy or trifluoromethanesulphonyloxy; or c) treating a hexahydrofuro[2,3-b]furan compound represented by the general formula IV wherein $R^1$, $R^2$, $R^3$, $R^4$, $R^5$, $R^6$, $R^7$, $R^8$, $R^9$, $R^{10}$ and r are as defined in general formula I and U is —$NH_2$, —$NH_2$, —$NH(C_1$–$C_6$ alkyl) or —$NH(CH_2CH_2$-$NMe_2)$ with both a compound of general formula VI

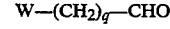

wherein W and q are as defined in general formula I, and potassium cyanide or sodium cyanide; or d) treating a substituted diamino compound of general formula VII

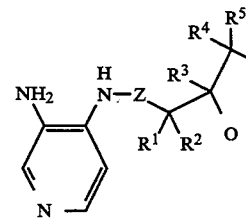

wherein $R^1$, $R^2$, $R^3$, $R^4$, $R^5$, $R^6$, $R^7$, $R^8$, $R^9$, $R^{10}$ and Z are as defined in general formula I, with acetic acid, or a suitable derivative thereof; and e) optionally after any of steps (a) to (d) converting a compound of general formula I so formed into another compound of general formula I.

The preferred reaction conditions for step (a) involve treatment of a compound of general formula III with a base (e.g. n-butyllithium, sodium hydride etc) in an aprotic solvent (e.g. tetrahydrofuran) to form an anion which is then reacted with a hexahydrofuro[2,3-b]furan derivative of general formula II. The above reactions can be effected at mild temperatures, typically between −78°°C. and 25° C.

The preferred reaction conditions for step (b) involve treatment of a hexahydrofuro[2,3-b]furan compound of general formula IV with a base (e.g. n-butyllithium, sodium hydride etc) in an aprotic solvent (e.g. tetrahydrofuran) to form an anion which is then reacted with a compound of general formula V. The above reactions can be effected at mild temperatures, typically between −78°°C. and 25° C.

The reaction of step (c) is a variation of the "Stecker synthesis" and the preferred reaction conditions involve use of a mixed organic/aqueous solvent system.

In step (d), derivatives of acetic acid that are suitable substrates for the reaction include acetyl halides, acetic anhydride, trialkylorthoesters of general formula VIII

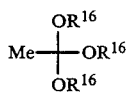

VIII wherein $R^{16}$ is —$C_1$–$C_6$ alkyl, or imino ether salts of general formula IX

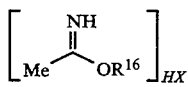

IX wherein $R^{16}$ is —$C_1$–$C_6$ alkyl and X is fluoride, chloride, bromide, or iodide. Trialkylorthoesters of general formula VIII and imino ether salts of general formula IX are available in the art or can be prepared by methods analogous to those known in the art.

Hexahydrofuro[2,3-b]furan derivatives of general formula II may be prepared by treatment of a lactol of general formula X

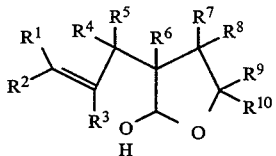

X wherein $R^1$, $R^2$, $R^3$, $R^4$, $R^5$, $R^6$, $R^7$, $R^8$, $R^9$, and $R^{10}$ are as defined in general formula I with a halogenating agent such as iodine, bromine, N-iodosuccinimide or N-bromosuccinimide in a suitable solvent (e.g. chloroform or acetonitrile) and in the presence or absence of a base (e.g. sodium hydrogen carbonate).

Lactols of general formula X may be prepared by the reduction of an allyl substituted lactone of general formula XI

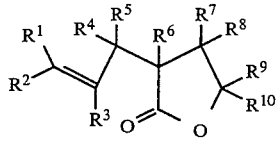

XI wherein $R^1$, $R^2$, $R^3$, $R^4$, $R^5$, $R^6$, $R^7$, $R^8$, $R^9$, and $R^{10}$ are as defined in general formula I, with a suitable reducing agent (e.g. diisobutylaluminium hydride) in an appropriate solvent (e.g. toluene).

Allyl substituted lactones of general formula XI may be prepared by methods known to those skilled in the art, which include the following procedures. The first method involves the treatment of a lactone of general formula XII

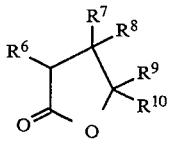

XII wherein $R^6$, $R^7$, $R^8$, $R^9$, and $R^{10}$ are as defined in general formula I, with a strong organic non-nucleophilic base (e.g. lithium diisopropylamide) in an appropriate aprotic solvent (e.g. tetrahydrofuran) followed by an allyl derivative of general formula XIII

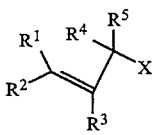

XIII wherein $R^1$, $R^2$, $R^3$, $R^4$ and $R^5$ are as defined in general formula I and X is fluoro, chloro, bromo, iodo, methanesulphonyloxy, p-toluenesulphonyloxy or trifluoromethanesulphonyloxy. Allyl derivatives of general formula XIII are available in the art or may be prepared by methods known to those skilled the art.

Lactones of general formula XII are available in the art or may be prepared by methods known to those skilled in the art, which include the following procedures. The first method involves cyclisation of hydroxy ester of general formula XIV

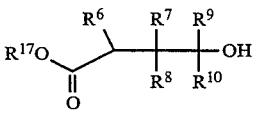

XIV wherein $R^6$, $R^7$, $R^8$, $R^9$ and $R^{10}$ are as defined in general formula I and $R^{17}$ is —$C_1$–$C_6$ alkyl, catalysed by a suitable acid (e.g. p-toluenesulphonic acid).

Hydroxy esters of general formula XIV, wherein $R^9$ is a hydrogen atom, may be prepared by the reduction of keto esters of general formula XV

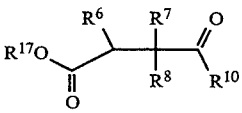

XV wherein R⁶, R⁷, R⁸ and R¹⁰ are as defined in general formula I and R¹⁷ is as defined above, with a suitable reducing agent (e.g. sodium borohydride).

Under certain conditions (sodium cyanoborohydride and hydrochloric acid in tetrahydrofuran at reflux) keto esters of general formula XV may be converted directly to lactones of general formula XII. Optically active enantiomers of hydroxy esters of general formula XIV may be obtained by utilising a chiral reducing agent (e.g. Bakers' yeast) for the reduction of keto esters of general formula XV. Keto esters of general formula XV are available in the art or may be prepared by methods analogous to those known in the art.

Hydroxy esters of general formula XIV may be prepared by a second method which involves treatment of an epoxide of general formula XVI

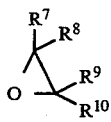   XVI wherein R⁷, R⁸, R⁹ and R¹⁰ are as defined in general formula I with an enolate derived by the treatment of an ester or amide derivative of general formula XVII

R⁶CHA   XVII wherein R⁶ is as defined in general formula I and A is CO₂C₁–C₆ alkyl or CON(C₁–C₆)₂. Lithium diisopropyl amide may be used as base to form the enolate in an aprotic solvent (e.g. tetrahydrofuran). The yield and stereoselectivity of the reaction may be altered by transmetallation of the enolate with an agent such as diethylaluminium chloride. Epoxides of general formula XVI and ester or amide derivatives of general formula XVII are available in the art or may be prepared by methods analogous to those known in the art.

In a second method lactones of general formula XII may be prepared by the treatment of an unsaturated ester of general formula XVIII

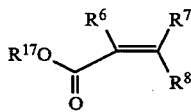   XVIII wherein R⁶, R⁷ and R⁸ are as defined in general formula I and R¹⁷ is as defined above, with a carbonyl compound of general formula XIX

O=CR⁹R¹⁰   XIX wherein R⁹, and R¹⁰ are as defined in general formula I, with samarium iodide in tetrahydrofuran. Unsaturated esters of general formula XVIII are available in the art or may be prepared by methods analogous to those known in the art.

Optionally after either of the above methods, a lactone of general formula XII may be converted into another lactone of general formula XII, in one or a plurality of the following methods:
i) by treatment of a lactone of general formula XII, wherein R⁷, R⁸, R⁹, and R¹⁰ are as defined in general formula I and R⁶ is a hydrogen atom with a strong organic non-nucleophilic base (e.g. lithium diisopropyl amide) in an appropriate aprotic solvent (e.g. tetrahydrofuran) followed by a compound of general formula XX

R⁶X   XX wherein R⁶ is as defined in general formula I and X is a leaving group such as chloro, bromo, iodo, methanesulphonyloxy, p-toluenesulphonyloxy or trifluoromethanesulphonyloxy; and/or
ii) by treatment of a lactone of general formula XII, wherein R⁶, R⁸, R⁹, and R¹⁰ are as defined in general formula I and R⁷ is a hydrogen atom with a strong organic non-nucleophilic base (e.g. lithium diisopropyl amide) in an appropriate aprotic solvent (e.g. tetrahydrofuran) followed by a compound of general formula XXI PhSeCl   XXI and subsequent treatment with hydrogen peroxide to yield an unsaturated lactone to which is added an appropriate organometallic reagent for example of general formula XXII (R⁷)₂CuLi   XXII wherein R⁷ is as defined in general formula I.

In a second method allyl substitued lactones of general formula XI may be prepared by the reaction of an epoxide of general formula XVI with an enolate derived by the treatment of an allyl substituted ester or amide compound of general formula XXIII

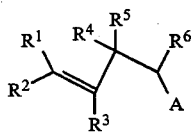   XXIII wherein R¹, R², R³, R⁴, R⁵ and R⁶ are as defined in general formula I and A is CO₂C₁–C₆ alkyl or CON(C₁–C₆ alkyl)₂. Lithium diisopropyl amide may be used as base to form the enolate in an aprotic solvent (e.g. tetrahydrofuran). The yield and stereoselectivity of the reaction may be altered by transmetallation of the enolate with an agent such as diethylaluminium chloride. Allyl substituted ester or amide compounds of general formula XXIII are available in the art or may be prepared by methods analogous to those known in the art.

Compounds of general formula III are available in the art or may be prepared by methods known to those skilled in the art.

Hexahydrofuro[2,3-b]furan compounds of general formula IV may be prepared by the reduction of a hexahydrofuro[2,3-b]furan derivative of general formula XXIV

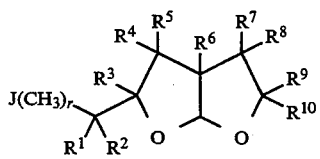   XXIV wherein R¹, R², R³, R⁴, R⁵, R⁶, R⁷, R⁸, R⁹, R¹⁰ and r are as defined in general formula I and J is an ester, thioester, amide or nitrile group with a suitable hydride reducing agent (e.g. lithium aluminium hydride).

Hexahydrofuro[2,3-b]furan derivatives of general formula XXIV, wherein J is nitrite and r is an integer of 0, may be prepared by the treatment of a hexahydrofuro[2,3-b]furan derivative of general formula II with either sodium or potassium cyanide.

Hexahydrofuro[2,3-b]furan derivatives of general formula XXIV, wherein J is a nitrite, ester or thioester and r is an integer of 1, may be prepared by the treatment of a hexahydrofuro[2,3-b]furan derivative of general formula II with a compound of general formula XXV $$J-CH_3 \qquad XXV$$

wherein J is as defined above, with a suitable strong organic non-nucleophilic base (e.g. lithium diisopropyl amide) in an appropriate aprotic solvent (e.g. tetrahydrofuran). Compounds of general formula XXV are available in the art.

Compounds of general formula V and VI are available in the art or may be prepared by methods known to those skilled in the art.

Substituted 1,2-diamines of general formula VII may be prepared by the reduction of a substituted 1,2-nitroamine of general formula XXVI

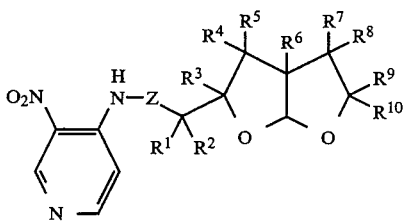

XXVI wherein $R^1$, $R^2$, $R^3$, $R^4$, $R^5$, $R^6$, $R^7$, $R^8$, $R^9$, $R^{10}$ and Z are as defined in general formula I, for example in the presence of hydrogen and a catalyst such as palladium or platinum.

Substituted 1,2-nitroamines of general formula XXVI may be prepared by the treatment of a nitro compound of general formula XXVII

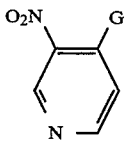

XXVII wherein G is halo or $-OC_1-C_6$ alkyl with an amino compound of general formula XXVIII

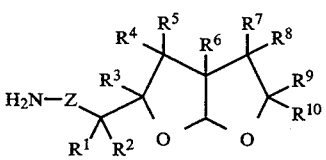

XXVIII wherein $R^1$, $R^2$, $R^3$, $R^4$, $R^5$, $R^6$, $R^7$, $R^8$, $R^9$, $R^{10}$ and Z are as defined in general formula I. Nitro compounds of general formula XXVII are available in the art or can be prepared by methods analogous to those known in the art. Certain amino compounds of general formula XXVIII can be prepared by treatment of a compound of general formula II with hexamethylenetetramine followed by treatment with ethanolic hydrochloric acid, by sequential treatment of a compound of general formula II with sodium azide followed by triphenylphosphine or by hydrogenation over a suitable catalyst, or by reduction of a general formula XXIV wherein J is nitrile with a suitable reducing agent (e.g. lithium aluminium hydride).

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae II, IV and VII are valuable intermediates in the preparation of compounds of general formula I, as are other novel compounds specifically or generically disclosed herein. According to a third aspect of the invention, there is therefore provided a compound of general formula II. According to a fourth aspect of the invention, there is provided a compound of general formula IV. According to a fifth aspect of the invention, there is provided a compound of general formula VII.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a sixth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an seventh aspect of the invention there is provided the use of a compound of general formula I in the preparation of an agent for the treatment or prophylaxis of PAF-mediated diseases, and/or the treatment of inflammatory disorders; such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a eighth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture, of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may, also be present. Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following example illustrates the invention, but is not intended to limit the scope in any way.

The following abbreviations have been used in the Examples:

DCM—Dichloromethane
DMF—N,N-Dimethylformamide
THF—Tetrahydrofuran

Unless otherwise stated $^1$H NMR and $^{13}$C NMR spectra were recorded on a Bruker AC-250 spectrometer at 250 MHz and 62.9 MHz respectively using CDCl$_3$ as a solvent and internal reference and are reported as delta ppm from TMS.

EXAMPLE 1

5-(4-Fluorophenyl)-2-(1H-2-methylbenzimidazol-1-ylmethyl)hexahydrofuro[2,3-b]furan

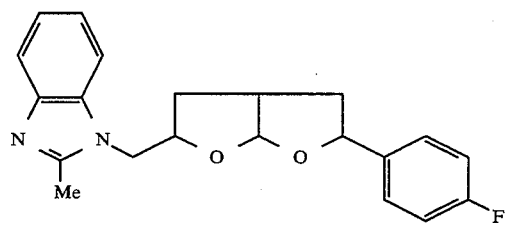

(a) 3-Allyl-5-(4-fluorophenyl)-γ-butyrolactone

A solution of lithium diisopropylamide (1.5M in THF: 56 ml, 84 mmol) was added dropwise to a stirred solution of 5-(4-fluorophenyl)-γ-butyrolactone (15.0 g, 83 mmol) in dry THF (100 ml) at −78°°C. under argon. The reaction mixture was stirred for 1 h at −78°°C. and allyl bromide (6.2 ml, 84 mmol) was added. The reaction mixture was allowed to warm slowly to room temperature and was stirred overnight. The mixture was concentrated under reduced pressure and the residue extracted into ethyl acetate and washed with water and brine. The organic extracts were dried over anhydrous sodium sulphate, filtered and concentrated to give a purple oil. The residue was purified by flash chromatography (silica: 5% ethyl acetate in hexane) to give the two separate diastereoisomers of 3-allyl-5-(4-fluorophenyl)-γ-butyrolactone ((3R*, 5S*)-diastereoisomer: 6.34 g, 37%) ((3R*, 5R*)-diastereoisomer: 2.90 g, 17%).

(3R*, 5S*)-3-Allyl-5-(4-fluorophenyl)-γ-butyrolactone: yellow amorphous solid.

Analysis calculated for $C_{13}H_{13}O_2F$; Required: C 70.89 H 5.92, Found: C 70.69 H 5.92.

i.r. (CDCl$_3$) 1760, 1670, 1380, 1300 cm$^{-1}$ $\delta_H$ 7.29 (2H, dd, J 8.7, 5.2 Hz), 7.03 (2H, dd, J 8.7, 8.7 Hz), 5.78 (1H, m), 3.32 (1H, dd, J 10.6, 5.7 Hz), 5.09 (1H, d, J 16.8 Hz), 5.07 (1H, d, J 9.1 Hz), 2.86 (1H, m), 2.75–2.59 (2H, m), 2.29 (1H, m), 1.85 (1H,m).

$\delta_C$ 177.52, 164.72, 160.70, 134.79, 134.22, 127.46, 127.33, 117.91, 115.84, 115.50, 78.82, 40.99, 37.18, 34.05.

(3R*, 5R*)-3-Allyl-5-(4-fluorophenyl)-γ-butyrolactone: colourless oil.

Analysis calculated for $C_{13}H_{13}O_2F$: Required: C 70.89 H 5.92, Found: C 70.74 H 6.00.

i.r. (CDCl$_3$) 1760, 1620,1580, 1380 cm$^{-1}$.

$\delta_H$ 7.29 (2H, dd, J 8.5, 5.4 Hz), 7.27 (2H, dd, J 8.6, 8.7 Hz), 5.80 (1H, m), 5.53 (1H, dd, J 7.5, 5.4 Hz), 5.18 (1H, d, J 7.5 Hz), 5.16 (1H, d, J 17.3 Hz), 2.78 (1H, m), 2.60 (1H, m), 2.55–2.38 (3H, m).

$\delta_C$ 178.30, 164.40, 160.46, 135.56, 135.50, 134.06, 126.90, 126.77, 118.04, 115.78, 115.43, 78.16, 38.55, 35.42, 34.40.

(b) 3-Allyl-5-(4-fluorophenyl)-γ-butyrolactol (i) A solution of diisobutylaluminium hydride (1M in toluene: 21.4 ml, 21.4 mmol) was added dropwise to a stirred suspension of (3R*, 5R*)-3-allyl-5-(4-fluorophenyl)-γ-butyrolactone (3.10 g, (3.10 g, 14.1 mmol) in dry toluene (50 ml) at −78°°C. under argon. The reaction mixture was stirred for 3 h at −78°°C. and benched by the addition of a slurry of sodium sulphate in water. The mixture was allowed to warm slowly to room temperature, stirred overnight and filtered through Celite. The filtrate was concentrated under reduced pressure and the residue extracted with ethyl acetate. The organic extracts were dried over anhydrous magnesium sulphate, filtered and concentrated to give crude (2RS, 3R*, 5R*)-3-allyl-5-(4-fluorophenyl)-γ-butyrolactol as a mixture of diastereoisomers (35:65) due to non-stereospecific reduction.

Colourless oil (2.85 91% yield).

$\delta_H$ 7.40 (1.3H, dd, J 8.5, 5.5 Hz) 7.24 (0.7H, dd, J 8.4, 5.4 Hz), 7.01 (2H, dd, J8.5, 8.5 Hz), 5.79 (1H, m), 5.53 (0.35H, m), 5.27 (0.65H, m), 5.14–4.96 (3H, m), 2.37–2.04 (4.4H, m), 1.94 (0.6H, m).

(ii) The same procedure was followed for the reduction of (3R*, 5S*)-3-allyl-5-(4-fluorophenyl)-γ-butyrolactone.

Yellow oil (85% yield).

$\delta_H$ 7.39 (0.7H, dd, J 8.53, 5.47 Hz), 7.31 (1.3H, dd, J 8.59, 5.40 Hz), 7.01 (2H, m) 5.92 5.70 (1H, m), 5.45 (0.35H, m), 5.37 (0.65H, m), 5.22 (1H, dd, J 9.65. 5.85 Hz), 5.14–4.97 (2H, m), 2.55–2.09 (4H, m), 1.78 (0.4H, m), 1.46 (0.6H, m).

(c) 5-(4-Fluorophenyl)-2-(iodomethyl)hexahydrofuro[2,3-b]furan

Iodine (12.99 51.6 mmol), was added to a stirred mixture of (2RS, 3R*, 5S*)-3-allyl-5-(4-fluorophenyl)-γ-butyrolactol (2.85 g, 12.9 mmol) (prepared in Step (b)(ii) above), and sodium hydrogen carbonate (2.16 g, 25.8 mmol) in dry acetonitrile (50 ml) at 9° C. under argon. The mixture was placed in the dark and stirred overnight at room temperature then partitioned between water and diethylether. The organic layer was separated and washed with aqueous sodium thiosulphate until colourless, followed by water and brine, dried over anhydrous magnesium sulphate, filtered and evaporated to give crude 5-(4-fluorophenyl)-2-(iodomethyl)-hexahydrofuro[2,3-b]furan. The iodoetherification reaction gives a 7:1 mixture of two diastereoisomers (2.19 g, 54%), (A) and (B) which were separated by flash chromatography (silica: 5% ethyl acetate in hexane).

Diastereoisomer (A): yellow oil.

i.r. (CDCl$_3$) 2850, 1610, 1510. 1150 cm$^{-1}$ 7.36 (2H, dd, J 8.4, 5.5 Hz), 7.03 (2H, dd, J 8.6, 8.3 Hz), 5.88 (1H, d, J 5.4 Hz), 4.91 (1H, dd, J 9.7, 6.2 Hz), 4.15 (1H, m), 3.36 (1H, dd, J 10.1, 5.2 Hz), 3.26 (1 H, dd, J 10.1, 7.5 Hz), 3.07 (1H, m), 2.01 (1 H, dd, J 12.7, 4.9 Hz), 1.80–1.53 (2H, m).

$\delta_C$ 164.14, 160.24, 137.34, 127.26, 127.12, 115.37, 115.03, 109.77, 80.22, 77.52, 76.90, 76.50, 44.06, 40.12, 38.71, 8.38.

The relative stereochemistry (2R*, 3aS*, 5R*, 6aR*) was determined by conducting $^1$H NMR decoupling experiments to assign proton chemical shifts followed by nOe difference spectroscopy:

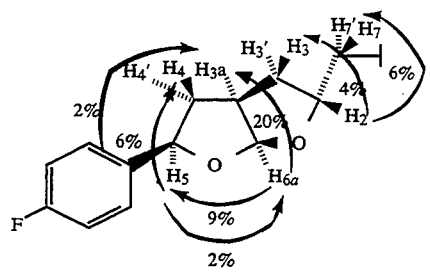

Diastereoisomer (B): yellow oil.

i.r. (CDCl$_3$): 2850, 1770, 1610, 1510, 1160 cm$^{-1}$ $\delta_H$ 7.38 (2H, dd, J 8.5, 5.4 Hz), 7.04 (2H, dd, J 8.7, 8.7 Hz), 5.82 (1H, d, J 5.4 Hz), 5.09 (1H, dd, J 7.6, 7.5 Hz), 4.28 (1H, m), 3.36 (1H, dd, J 9.8, 5.4 Hz), 3.31 (1H, dd, J 9.8, 7.9 Hz), 2.98 (1H, m), 2.56 (1H, m), 2.32 (1H, m), 1.81 (1H, m), 1.58 (1H, m).

$\delta_C$ 163.96, 160.05, 137.81, 127.36. 127.22, 115.25, 114.91, 110.50, 81.47, 80.87, 43.85, 40.68, 36.93, 9.42.

The relative stereochemistry (2R*, 3aR*, 5S*, 6aS*) was determined by conducting $^1$H NMR decoupling experiments to assign proton chemical shifts followed by nOe difference spectroscopy:

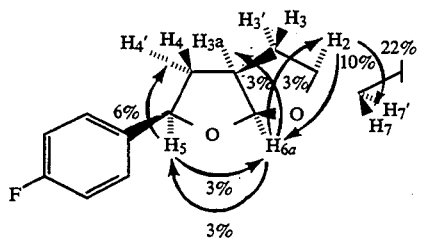

Iodine (10.02 g, 39.8 mmol) was added to a stirred mixture of (2RS, 3R*, 5R*)-3-allyl-5-(4-fluorophenyl)-γ-butyrolactol (2.20 g, 9.9 mmol) (prepared in Step (b)(i) above) and sodium hydrogen carbonate (1.67 g, 19.9 mmol) in dry acetonitrile (50 ml) at 0° C. under argon. The mixture was placed in the dark and stirred for 6 h at room temperature then partitioned between water and diethyl ether. The organic layer was separated and washed with aqueous sodium thiosulphate until colourless, water and brine, dried over anhydrous magnesium sulphate, filtered and evaporated to give crude 5-(4-fluorophenyl)-2-(iodomethyl)hexahydrofuro[2,3-b]furan as a brown oil. The iodoetherification reaction gives a 1:1 mixture of two diastereoisomers (2.2 g, 73%), (C) and (D) isomers which were separated by flash chromatography (silica: 5% ethyl acetate in hexane).

Diastereoisomer (C): yellow oil.

i.r. (CDCl$_3$): 2850, 1770, 1610. 1510, 1160 cm$^{-1}$ $\delta_H$ 7.33 (2H, dd, J 8.6, 5.5 Hz), 7.01 (2H, dd, J 8.7, 8.6 Hz), 5.91 (1H, d, J 5.4 H,), 5.17 (1H, dd, J 11.0, 4.8 Hz), 3.92 (1H, m), 3.42 (1H, dd, J 10.1, 4.7 Hz), 3.34 (1 H, dd, J 10.0, 6.8 Hz), 3.08 (1 H, m), 2.45 (1H, m), 2.1 1 (1H, dd, J 12.6, 4.8 Hz), 1.86 (1 H, m), 1.57 (1H, m).

$\delta_C$ 164.18, 160.27, 136.19, 127.54, 127.61, 115.31, 114.97, 109.60. 78.40, 77.84, 43.88, 41.31, 37.71, 8.97.

The relative stereochemistry (2R*, 3aR*, 5R*, 6aS*) was determined by conducting $^1$H NMR decoupling experiments to assign proton chemical shifts followed by nOe difference spectroscopy:

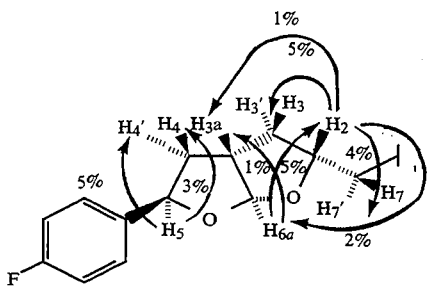

Diastereoisomer (D): white waxy solid.

Analysis calculated for $C_{13}H_{14}O_2FI$: Required: C 44.84 H 4.05, Found: $C_{44.94}$ H 3.97.

i.r. (CDCl₃): 2985, 2880, 1770, 1610, 1510, 1150 cm⁻¹
$\delta_H$ 7.29 (2H, dd, J 8.7, 5.6 Hz), 7.02 (2H, dd, J 8.7, 8.7 Hz), 6.02 (1H, d, J 5.0 Hz), 5.11 (1 H, dd, J 10.2. 5.7 Hz), 4.32 (1 H, m), 3.34 (1H, dd, J 10.1, 4.4 Hz), 3.21 (1 H, dd, J 10.0, 6.8 Hz), 3.15 (1H, m), 2.20–1.89 (4H, m).

$\delta_C$ 164.15, 160.23, 136.83, 127.46, 127.34, 115.36, 115.03, 109.77, 80.22, 79.12, 43.44, 41.72, 39.06, 9.41.

The relative stereochemistry (2R*, 3aS*, 5S*, 6aR*) was determined by conducting ¹H NMR decoupling experiments to assign proton chemical shifts followed by nOe difference spectroscopy:

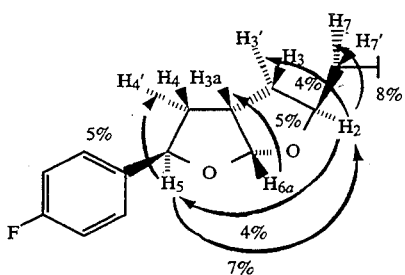

(d) (2R*, 3aS*, 5S*, 6aR*)-5-(4-Fluorophenyl)-2-(1H-2-methylbenzimidazol-1-ylmethyl)hexahydrofuro[2,3-b]furan

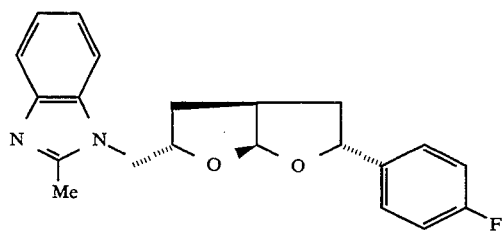

Potassium hydroxide (0.38 g, 6.8 mmol) and TDA-1 (catalytic amount) were added to a stirred suspension of 2-methylbenzimidazole (0.89 g, 6.8 mmol) in dry acetonitrile (40 ml). The reaction mixture was stirred for 1 h at 80°°C. and a solution of (2R*, 3aS*, 5S*, 6aR*)-5-(4-fluorophenyl)-2-(iodomethyl)-hexahydrofuro[2,3-b]furan (Diastereoisomer D) (2.05 g, 6.8 mmol) in dry acetonitrile (10 ml) was added at 40° C. The reaction mixture was refluxed overnight and the solvent removed under low pressure. The residue was extracted with DCM, filtered through celite and concentrated to a yellow oil. The residue was purified by flash chromatography (silica: 3% ethanol in DCM containing 1% triethylamine) to give (2R*, 3aS*, 5S*, 6aR*)-5-(4-fluorophenyl)-2-(1H-2-methylbenzimidazol-1-ylmethyl)hexahydrofuro[2,3-b]furan as a yellow oil (150 mg, 6%) which was recrystallised from ethyl acetate and diisopropyl ether to give a yellow solid.

Elemental analysis for $C_{21}H_{21}N_2O_2F$: Required: C 71.21 H 6.17 N 7.80, Found: C 71.16 H 6.17 N 7.80.

i.r. (CDCl₃) : 3020, 2850, 1610, 1520, 1450, 1150 cm⁻¹.

$\delta_H$ 7.68 (1H, m), 7.32 (1H, m), 7.23 (4H, m), 7.12 (2H, dd, J 8.7, 8.7 Hz), 5.87 (1 H, dd, J 5.0 Hz), 5.05 (1 H, dd, J 9.9, 5.9 Hz), 4.61 (1 H, m), 4.34 (1 H, dd, J 15.2, 3.8 Hz), 4.18 (1 H, dd, J 15.2, 5.2 Hz), 2.97 (1 H, m), 2.67 (3H, s), 2.16–1.83 (4H, m).

$\delta_C$ 164.09, 160.17, 152.38, 142.15, 136.74, 135.47, 127.28, 127.15, 122.11, 121.98, 118.89, 115.32, 114.97, 109.36, 109.00, 80.48, 78.69, 47.13, 43.07, 41.28. 35.87, 14.13.

(e) (2R*, 3aS*, 5R*, 6aR*)-5-(4-Fluorophenyl)-2-(1H-2-methylbenzimidazo-1-ylmethyl)hexahydrofuro[2,3-b]furan

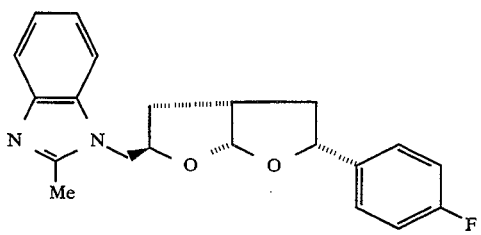

(2R*, 3aS*, 5R*, 6aR*)-5-(4-Fluorophenyl)-2-(iodomethyl)hexahydrofuro[2,3-b]furan (Diastereoisomer A) was reacted with 2-methylbenzimidazole and gave (2R*, 3aS*, 5R*, 6aR*)-5-(4-fluorophenyl)-2-(1H-2-methylbenzimidazol-1-ylmethyl)hexahydrofuro[2,3-b]furan under the conditions described above in Step (d).

Yellow oil (320 mg, 14%).

i.r. (CDCl₃) 3020, 2850, 1610, 1520, 1450, 1150 cm⁻¹
$\delta_H$ 7.69 (1H, m), 7.24 (5H, m), 6.96 (2H, dd, J 8.8, 8.7 Hz), 5.70 (1H, d, J 5.4 Hz), 4.82 (1H, dd, J 9.8, 6.0 Hz), 4.45 (1H, m), 4.38 (1H, dd, J 15.1, 3.4 Hz), 4.21 (1H, dd, J 15.1, 4.8 Hz), 2.92 (1H, m), 2.63 (3H, s), 2.49 (1H, m), 1.80–1.45 (3H, m).

$\delta_C$ 164.12, 160.22, 152.58, 142.28, 136.87, 135.64, 127.19, 127.05, 122.09, 121.96, 118.92, 115.35, 115.01, 109.45, 108.79, 79.86, 76.42, 46.19, 43.57, 39.69, 35.27, 14.19.

EXAMPLE 2

5-(4-Fluorophenyl)-2-(1H-2-methylimidazo[4,5-c]pyrid-1-ylmethyl)hexahydrofuro[2,3-b]furan

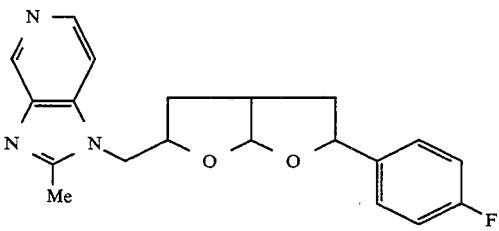

Sodium hydride (60% dispersion in oil: 0.26 g, 6.5 mmol) was added to a stirred solution of 2-methylimidazo[4,5-c]pyridine (0.80 g, 6.1 mmol) in a mixture of dry DMF (10 ml) and dry THF (30 ml)

under argon at room temperature. After 1 h a solution of (2R*, 3aS*, 5S*, 6aR*)-5-(4-fluorophenyl)-2-(iodomethyl)hexahydrofuro[2,3-b]furan (2.10 g, 6.1 mmol) in dry THF (5 ml) was added. The mixture was stirred overnight and the solvent removed under reduced pressure. The residue was extracted with ethyl acetate (100 ml) and the organic extracts washed with water (100 ml) and brine 100 ml), dried over anhydrous magnesium sulphate filtered and evaporated. The residue was purified by column chromatography (silica: 4% methanol in DCM) to give 5-(4-fluorophenyl)-2-(1H-2-methylimidazo[4,5-c]pyrid-1-yl-methyl)hexahydrofuro[2,3-b]furan (25 mg, 1%) as a yellow oil.

$\delta_N$ 8.99 (1H, s), 8.40 (1H, d, J 5.5 Hz), 7.40 (3H, m), 7.06–6.94 (2H, m), 5.88 (1 H, d, J 5.0 Hz), 5.07 (1H, dd, J 10.1, 5.8 Hz), 4.61 (1H, m), 4.47–4.15 (2H, m), 3.01 (1H, m), 2.71 (3H, s), 2.44–1.63 (4H, m).

EXAMPLE 3

2-(4-Fluorophenyl)-5-(2(1H-2-methylimidazo[4,5-c]pyrid-1-yl)ethyl)hexahydrofuro[2,3-b]furan

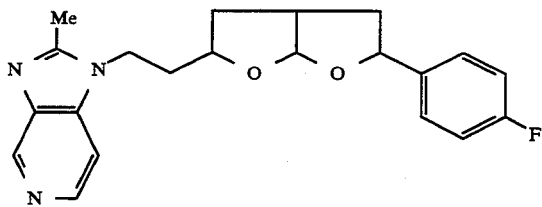

(a) 2-(Cyanomethyl)-5-(4-fluorophenyl)hexahydrofuro[2,3-b]furan

To a stirred solution of 5-4-fluorophenyl)-2-(iodomethyl)hexahydrofuro[2,3-b]furan (mixture of 4-diastereoisomers) (1.2 g, 4.0 mmol) in dry DMF (20 ml) was added potassium cyanide (1.03 g, 15.9 mmol). The mixture is stirred at room temperature for 9 days. The sovent was removed under reduced pressure and the residue taken up in ethyl acetate, washed with water (100 ml) and brine (100 ml), dried over anhydrous sodium sulphate, filtered and concentrated. The residue was purified by column chromatography to give 2-(cyanomethyl)-5-(4-fluorophenyl)hexahydrofuro[2,3-b]furan (300 mg, 30%) as a colourless oil.

$\delta_H$ 7.39–7.24 (2H, m), 7.08–6.93 (2H, m), 6.00–5.69 (1H, m), 5.12–4.82 (1H, m), 4.52–4.04 (1H, m), 3.27–0.98 (7H, m).

(b) 5-(2-Aminoethyl)-2-(4-fluorophenyl)hexahydrofuro[2,3-b]furan

Lithium aluminium hydride (92 mg, 2.5 mmol) was added to a stirred solution of 2-(cyanomethyl)-5-(4-fluorophenyl)hexahydrofuro[2,3-b]furan (300 mg, 1.2 mmol) in dry THF. The reaction mixture was stirred overnight and water (0.9 ml), 15% sodium hydroxide (0.9 ml) and water (2.7 ml) are added in succession. The white percipitate was filtered off and the solvent removed under reduced pressure to give crude 5-(2-aminoethyl)-2-(4-fluorophenyl)hexahydrofuro[2,3-b]furan which is used directly in the next step.

(c) 2-(4-Fluorophenyl)-5-(2-(N-3-nitropyrid-4-ylaminoethyl)hexahydrofuro[2,3-b]furan 4Chloro-3-nitropyridine (160 mg, 1.0 mmol) is added to a stirred solution of 5-(2-aminoethyl)-2-(4-fluorophenyl)hexahydrofuro[2,3-b]furan (200 mg, 0.8 mmol) and triethylamine (1.0 ml) in chloroform (15 ml) at ambient temperature. The reaction mixture is stirred overnight, then washed with water, dried over anhydrous magnesium sulphate, filtered and the solvent removed under reduced pressure to leave an orange oil. This is purified by chromatography over silica (1:1 ethyl acetate/hexane) to give 2-(4-fluorophenyl)-5-(2-(N-3-nitropyrid-4-ylaminoethyl)hexahydrofuro[2,3-b]furan (175 mg, 59%) as a yellow amorphous solid.

$\delta_H$ 9.24 (1H, s), 8.61–8.56 (1H, br m), 8.26 (1H, d, J 5.9 Hz), 7.40–7.24 (2H, m), 7.08–6.90 (2H, m), 5.98–5.67 (1H, m), 5.13–4.83 (1H, m), 4.54–4.00 (1H, m), 3.25–0.97 (10H, m).

(d) 5-(2-(N-3-Aminopyrid-4-ylaminoethyl)-2-(4-fluorophenyl)hexahydrofuro[2,3-b]furan A solution of 2-(4-fluorophenyl)-5-(2-(N-3-nitropyrid-4-ylaminoethyl)hexahydrofuro[2,3-b]furan (175 mg, 0.44 mmol) in ethanol (5 ml) is hydrogenated at 120 p.s.i. overnight in the presence of 10% palladium in charcoal. The catalyst is removed by filtration through GF/F filter paper, and the filtrate evaporated under reduced pressure to give 5-(2-(N-3-aminopyrid-4-ylaminoethyl)-2-(4-fluorophenyl)hexahydrofuro[2,3-b]furan (145 mg, 91%) as a green oil.

$\delta_H$ 7.83–7.79 (2H, br m), 7.39–7.24 (2H, m), 7.10–6.95 (2H, m), 6.00–5.67 (1H, m), 5.10–4.82 (1H, m), 4.53–4.02 (1H, m), 3.27–0.99 (12H, m).

(e) 5-(4-Fluorophenyl)-2-(2(1H-2-methylimidazo[4,5-c]pyrid-1-yl)ethyl)-hexahydrofuro[2,3-b]furan 2-(2-(N-3-Aminopyrid-4-ylaminoethyl)-5-(4-fluorophenyl)hexahydrofuro[2,3-b]furan (140 mg, 0.41 mmol) is refluxed overnight in acetic anhydride (5 ml). The reaction mixture is allowed to cool, then methanol added cautiously until effervescence ceased. The volatiles are removed under reduced pressure and the residue partitioned between saturated sodium hydrogen carbonate solution and ethyl acetate. The organic portion is washed with saturated aqueous sodium hydrogen carbonate, and water, dried over anhydrous sodium sulphate, filtered and concentrated to a brown oil. The residue is purified by medium pressure liquid chromatography (silica: 3% methanol in DCM plus trace of triethylamine) to give 5-(4-fluorophenyl)-2-(2(1H-2-methylimidazo[4,5-c]pyrid-1-yl)ethyl)hexahydrofuro[2,3-b]furan as a pale yellow oil (78 mg, 52%).

$\delta_H$ 9.00 (1H, s), 8.33 (1H, d, J 5.5 Hz), 7.39–7.24 (2H, m), 7.15–6.92 (3H, m), 6.00–5.66 (1H, m), 5.12–4.80 (1H, m). 4.51–3.98 (1H, m), 2.66 (3H, s), 3.27–0.98 (9H, m).

EXAMPLES 4 TO 9

The compounds of Examples 4 to 9 are prepared by the method of Example 1 Steps (a)–(c) and Example 3 Steps (a)–(e) starting from the appropriate butyrolactone in lieu of 5-(4-fluorophenyl)-γ-butyrolactone. The diastereoisomers formed in the alkylation step and iodoetherification step are not separated. In each case the final compounds are obtained as mixtures of diastereoisomers as indicated by NMR spectroscopy.

4. 2-(4-Methoxyphenyl)-5-(2(1H-2-methylimidazo[4,5-c]pyrid-1-yl)ethyl)hexahydrofuro[2,3-b]furan, 5. 2-(3,4-Dimethoxyphenyl)-5-(2(1H-2-methylimidazo[4,5-c]pyrid-1-yl)ethyl)hexahydrofuro[2,3-b]furan, 6. 2-(3,4-Dichlorophenyl)-5-(2(1H-2-methylimidazo[4,5-c]pyrid-1-yl)ethyl)hexahydrofuro[2,3-b]furan, 7. 2-(3-Chloro-4-methoxyphenyl)-5-(2(1H-2-methylimidazo[4,5-c]pyrid-1-yl)ethyl)hexahydrofuro[2,3-b]furan, 8. 2-(2,4,6-Triisopropylphenyl)-5-(2(1H-2-methylimidazo[4,5-c]pyrid-1-yl)ethyl)hexahydrofuro[2,3-b]furan, 9. 2-(2(1H-2-Methylimidazo[4,5-c]pyrid-1-yl)ethyl)-5-pentadecylhexahydrofuro[2,3-b]furan.

EXAMPLE 10

2-(4-Fluorophenyl)-5-[N-(3-pyridylcyanomethyl)aminoethyl]hexahydrofuro[2,3-b]furan

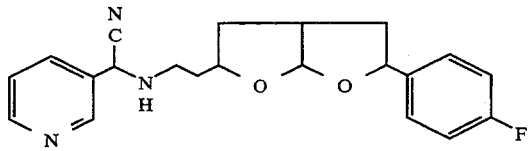

A solution of nicotinaldehyde (110 mg, 1.0 mmol) in methanol (2 ml) is added to a stirred solution of 5-(4-Fluorophenyl)-2-(2-aminoethyl)hexahydrofuro[2,3-b]furan (250 mg, 1.0 mmol) and potassium cyanide (65 mg, 1.0 mmol) in water (2 ml) and 1M phosphate buffer solution (pH 7:2 ml). The reaction mixture is stirred for 24 h and partitioned between water (10 ml) and ethyl acetate (20 ml). The organics are dried over anhydrous sodium sulphate, filtered and concentrated. The residue is purified by chromatography (silica gel: 2% methanol in DCM) to give 2-(4-fluorophenyl)-5-[N-(3-pyridylcyanomethyl)aminoethyl]hexahydrofuro[2,3-b]furan as a colourless oil.

$\delta_H$ 8.78 (1H, br s), 8.61 (1H, dd, J 4.8, 1.3 Hz), 7.87 (1H, br d, J 6.4 Hz) 9.40–7.24 (3H, m), 7.08–6.93 (2H, m), 5.99–5.65 (1H, m), 5.14–4.80 (2H, m), 4.50–4.00 (1H, m), 3.27–0.98 (10H, m).

EXAMPLE 11

5-[N-((2-Methyl)-3-pyridylcyanomethyl)aminoethyl]-2-(3,4,5-trimethoxyphenyl)hexahydrofuro[2,3-b]furan

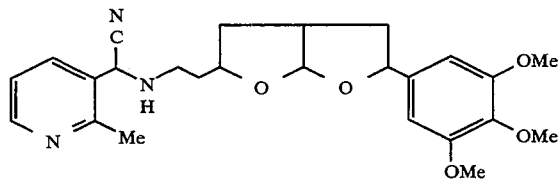

5-[N-((2-Methyl)-3-pyridylcyanomethyl)aminoethyl]-2-(3,4,5-trimethoxyphenyl)hexahydrofuro[2,3-b]furan is prepared by the procedure of Example 12 employing 2 pyridine-3-carboxaldehyde and 5-(2-aminoethyl)-2-(3,4,5-trimethoxyphenylphenyl)hexahydrofuro[2,3-b]furan as starting materials. 5-(2-Aminoethyl)-2-(3,4,5-trimethoxyphenylphenyl)hexahydrofuro[2,3-b]furan is prepared by the method of Example 1 Steps (a)–(c) and Example 1 Steps (a) and (b), starting from 5-(3,4,5-trimethoxyphenyl)-γ-butyrolactone. 2-Methylpyridine-3-carboxaldehyde is prepared from 2-(chloromethyl)pyridine hydrochloride by a procedure analogous to that reported in the literature (Weinreb, S. et al., J. Am. Chem. Soc. 104(2), 536–544 (1982)).

EXAMPLES 12–13

The compounds of Examples 12 and 13 are prepared by the method of Example 10 employing the appropriate secondary amine as starting material. The secondary amines are prepared by alkylation of the requisite amine with 5-(4-fluorophenyl)-2-(iodomethyl)hexahydrofuro[2,3-b]furan.

12. 5-(4-Fluorophenyl)-2-[N-(3-pyridylcyanomethyl)aminomethyl]hexahydrofuro[2,3-b]furan 13. 5-(4-Fluorophenyl)-2-[N-(3-pyridylcyanomethyl)-N-(N',N'-dimethylaminoethyl)aminomethyl]hexahydrofuro[2,3-b]furan

EXAMPLE 14

Inhibition of [³H]-PAF binding to washed human platelet membranes

In common with the compounds of the invention (general formula I) those of Examples 1–13 it PAF-induced functions at both cellular and tissue levels by inhibition of PAF binding to its specific receptor site. The inhibition of [³H]-PAF binding to washed human platelet membranes by representative compounds was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supenatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5mM MgCl₂, 2 mM EDTA, pH 7.0), snap freezed in liquid N₂ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained [³H]-PAF (0.5 nM; 1—O-[³H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgCl₂, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

% Inhibition = [(TB−TBA)/SB] × 100 where the specific binding SB = TB − NSB

The Table lists results from this assay for inhibition of [$^3$H]-PAF receptor binding for illustrative examples of the compounds of this invention.

TABLE

| Results for inhibition of [$^3$H]-PAF receptor binding | |
|---|---|
| Example | Inhibition of [$^3$H]-PAF binding IC$_{50}$ μM |
| 1(d) | 8.0 |
| 1(e) | 0.45 |
| 2 | 0.24 |

I claim:
1. A compound of formula I;

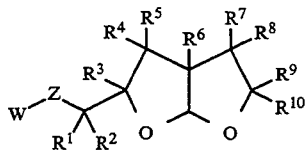

wherein:
W represents pyrid-3-yl, benzimidazol-1-yl, and imidazo[4,5-c]pyrid-1-yl optionally substituted with one or more substituents selected from methyl, methoxy, halo, —CF$_3$ and —CN;
Z represents
  a) a bond;
  b) a divalent alkanediyl group from 1 to 4 carbon atoms which may be a straight or branched-chain, wherein the said group is either unsubstituted or substituted by one or more substituents selected from hydroxy, —OC$_1$-C$_6$ alkyl, —SC$_1$-C$_6$ alkyl, —CN and halo;
  c) a divalent alkanediyl or alkynediyl group from 2 to 4 carbon atoms which may be a straight or branched-chain, wherein the said group is either unsubstituted or substituted by one or more substituents selected from hydroxy, —OC$_1$-C$_6$ alkyl, —SC$_1$-C$_6$ alkyl, —CN and halo;
  d) a —(CH$_2$)$_q$U(CH$_2$)$_r$— group, optionally substituted by —CN, wherein q is an integer from 0-2, r is an integer from 0-2 and U represents a sulphur atom, an oxygen atom, a —N(H)— group, a —N(C$_1$-C$_6$ alkyl)— group, a —N(CH$_2$CH$_2$NMe$_2$)— group or a —N(C(=O)C$_1$-C$_6$ alkyl)— group;

R$^1$, R$^2$, R$^3$, R$^4$, R$^5$, R$^6$, R$^7$, R$^8$ and R$^9$ each independently represents hydrogen, halo, —OH, —C$_1$-C$_6$ alkyl;
R$^{10}$ presents —C$_1$-C$_{18}$ alkyl, —C$_2$-C$_{18}$ alkenyl, —C$_3$-C$_8$ cycloalkyl, —C$_4$-C$_8$ cycloalkenyl, a —V group, where V is a

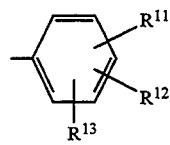

group wherein each of R$^{11}$, R$^{12}$ and R$^{13}$ is independently hydrogen, —C$_1$-C$_6$ alkyl, —OC$_1$-C$_6$ alkyl, —SC$_1$-C$_6$ alkyl, halo, —CN, —NO$_2$, —SOC$_1$-C$_6$ alkyl, —SO$_1$-C$_6$ alkyl, —SO$_2$(CH$_2$)$_1$-CH$_2$OH, —SO$_2$NH$_2$, —CO$_2$H, —CO$_2$-C$_1$-C$_6$ alkyl, —CHO, —COC$_1$-C$_6$ alkyl, —CH$_2$OH, —OH, benzyl, benzoyl, —CF$_3$, —CONH$_2$, —NHCOC$_1$-C$_6$ alkyl, or an —NR$^{14}$R$^{15}$ group wherein each of R$^{14}$ and R$^{15}$ is independently hydrogen or —C$_1$-C$_6$ alkyl;
or a pharmaceutically or veterinarily acceptable acid addition salt or hydrate thereof.

2. A compound as claimed in claim 1, in which W represents an unsubstituted pyrid-3-yl group, benzimidazol-1-yl, or imidazo[4,5-c]pyrid-1-yl group.

3. A compound as claimed in claim 1, wherein Z represents a bond, a divalent alkanediyl group or a —(CH$_2$)$_q$U(CH$_2$)$_r$— (substituted by —CN) group wherein q represents an integer of 1, r represents an integer of 0 or 1 and U represents a —N(H)— group, a —N(C$_1$-C$_6$ alkyl)— group or a —N(CH$_2$CH$_2$NMe$_2$)— group.

4. A compound as claimed in claim 1, wherein one or more of R$^1$, R$^2$, R$^3$, R$^4$, R$^5$, R$_6$, R$_7$, R$^8$ and R$^9$ is hydrogen.

5. A compound as claimed in claim 1, wherein R$^{10}$ represents a —C$_1$-C$_{18}$ alkyl group or a V group where V is a

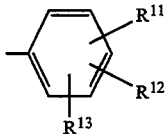

group wherein R$^{11}$ represents a —C$_1$-C$_6$ alkyl group, halo, or a —OC$_1$-C$_6$ alkyl group, R$^{12}$ represents hydrogen, a —C$_1$-C$_6$ alkyl group, halo or a —OC$_1$-C$_6$ alkyl group, and R$^{13}$ represents hydrogen, a —C$_1$-C$_6$ alkyl group of a 6. A compound selected from the group consisting of:
5-(4-Fluorophenyl)-2-(1H-2-methylbenzimidazol-1-ylmethyl)hexahydrofuro[2,3-b]furan,
5-(4-Fluorophenyl)-2-(1H-2-methylimidazo[4,5-c]pyrid-1-ylmethyl)hexahydrofuro[2,3-b]furan,
2-(4-Fluorophenyl)-5-(2(1H-2-methylimidazo[4,5-c]pyrid-1-yl)ethyl)hexahydrofuro[2,3-b]furan,
2-(4-Methoxyphenyl)-5-(2(1H-2-methylimidazo[4,5-c]pyrid-1-yl)ethyl)hexahydrofuro[2,3-b]furan, 2-(3,4-Dimethoxyphenyl)-5-(2(1H-2-methylimidazo[4,5-c]pyrid-1-yl)ethyl)hexahydrofuro[2,3-b]furan, 2-(3,4-Dichlorophenyl)-5-(2(1H-2-methylimidazo[4,5-c]pyrid-1-yl)ethyl)hexahydrofuro[2,3-b]furan, 2-(3-Chloro-4-methoxyphenyl)-5-(2(1H-2-methylimidazo[4,5-c]pyrid-1-yl)ethyl)hexahydrofuro[2,3-b]furan, 2-(2,4,6-Triisopropylphenyl)-5-(2(1H-2-methylimidazo[4,5-c]pyrid-1-yl) -ethyl)hexahydrofuro[2,3-b]furan, 2-(2(1H-2-Methylimidazo[4,5-c]pyrid-1-yl)ethyl)-5-pentadecylhexahydrofuro[2,3-b]furan, 2-(4-Fluorophenyl)-5-[N-(3-pyridylcyanomethyl)aminoethyl]hexahydrofuro[2,3-b]furan, 5-[N-(2-Methyl)-3-pyridylcyanomethyl)aminoethyl]-2-(3,4,5-trimethoxyphenyl)hexahydrofuro[2,3-b]furan, 5-(4-Fluorophenyl)-2-[N-(3-pyridylcyanomethyl)aminomethyl]hexahydrofuro[2,3-b]furan, and 5-(4-Fluorophenyl)-2-[N-(3-pyridylcyanomethyl)-N-(N',N'-dimethylaminoethyl)aminomethyl]hexahydrofuro[2,3-b]furan, and acid addition salts of such compounds.

7. A pharmaceutical or veterinary formulation comprising a compound as claimed in claim 1, and a pharmaceutically and/or veterinarily acceptable carrier.

8. A method for the treatment of diseases or conditions mediated by platelet activating factor, the method comprising administering to a patient effective amount of a compound as claimed in claim 1.

* * * * *